(12) United States Patent
Hermansson et al.

(10) Patent No.: US 7,413,079 B2
(45) Date of Patent: Aug. 19, 2008

(54) SINGLE WRAP FOR ABSORBENT PRODUCTS

(75) Inventors: Sofia Hermansson, Västra Frölunda (SE); Anders Stenberg, Onsala (SE); Kent Hermansson, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 403 days.

(21) Appl. No.: 10/886,581

(22) Filed: Jul. 9, 2004

(65) Prior Publication Data

US 2005/0029144 A1 Feb. 10, 2005

Related U.S. Application Data

(60) Provisional application No. 60/485,753, filed on Jul. 10, 2003.

(51) Int. Cl.
*B65D 85/16* (2006.01)

(52) U.S. Cl. .................. 206/440; 206/494; 206/812

(58) Field of Classification Search ............ 206/210, 206/440, 441, 494, 812; 604/385.02
See application file for complete search history.

(56) References Cited

U.S. PATENT DOCUMENTS

| | | | | |
|---|---|---|---|---|
| 2,676,702 A | * | 4/1954 | Whitefoot, Jr. | 206/440 |
| 3,017,990 A | * | 1/1962 | Singerman | 206/440 |
| 3,062,371 A | * | 11/1962 | Patience | 206/440 |
| 3,338,019 A | * | 8/1967 | Trewella et al. | 206/440 |
| 3,973,567 A | * | 8/1976 | Srinivasan et al. | 206/440 |
| 5,445,454 A | * | 8/1995 | Barkhorn | 206/440 |
| 5,474,818 A | * | 12/1995 | Ulrich et al. | 206/447 |
| 6,015,934 A | | 1/2000 | Lee et al. | |
| 6,036,679 A | | 3/2000 | Balzar et al. | |
| 6,041,928 A | | 3/2000 | Jousinen et al. | |
| 6,299,607 B1 | * | 10/2001 | Osborn et al. | 206/440 |
| 6,500,160 B2 | * | 12/2002 | Mizutani et al. | 604/385.02 |
| 2003/0004089 A1 | | 1/2003 | Huber et al. | |

FOREIGN PATENT DOCUMENTS

| | | |
|---|---|---|
| DE | 11 66 543 B | 3/1964 |
| DE | 37 20 809 A1 | 2/1988 |
| DE | 39 39 679 A1 | 5/1991 |
| EP | 0 012 275 A1 | 6/1980 |
| EP | 0 450 247 A2 | 10/1991 |
| GB | 2 017 505 | 10/1979 |
| GB | 2 221 667 | 2/1990 |
| GB | 2 249 295 | 5/1992 |
| WO | 88/10219 A1 | 12/1988 |
| WO | 97/16143 | 5/1997 |
| WO | 01/43674 A1 | 6/2001 |

* cited by examiner

*Primary Examiner*—Luan K Bui
(74) *Attorney, Agent, or Firm*—Buchanan Ingersoll & Rooney PC (57) ABSTRACT

A packing wrap for enclosing an individual packed absorbent article, such as a sanitary towel, a panty liner or an incontinence pad, including a first material piece arranged over the first surface of the absorbent article and a second material piece arranged over the second surface of the absorbent article, an opening location having a longitudinal extent, and a region capable of tactile detection of the opening location, the region being arranged adjacent to the opening location. The region has a longitudinal extent, and is arranged essentially parallel to the longitudinal extent of the opening location.

5 Claims, 7 Drawing Sheets

SINGLE WRAP FOR ABSORBENT PRODUCTS

CROSS-REFERENCE TO RELATED APPLICATIONS

The present application claims the benefit of U.S. Provisional Application No. 60/485,753, filed in the United States on Jul. 10, 2003, the entire contents of which are hereby incorporated herein by reference.

TECHNICAL FIELD

The invention relates to a packing wrap for a packing-configured individually packed absorbent article, such as a sanitary towel, a panty liner, or an incontinence pad.

BACKGROUND ART

It is advantageous for several reasons to pack single absorbent articles of the above-mentioned kind in the introduction in individual packing wraps. In this way, small, handy packs are obtained, which can easily and conveniently be carried, for example in a handbag, or in a pocket, and from which an article can be removed when necessary. Such individual packs ensure that the article is protected against soiling and crumpling until use and are therefore greatly appreciated by users. With suitable design of the packing wraps, these can also serve as wrappers for used articles, which can thus be disposed of in a hygienic and aesthetically acceptable way.

A common way of individually packing absorbent articles is first to fold them together into a smaller format and then to wrap them in a thin packing wrap made of plastic or paper. Such a packing wrap often consists of a rectangular material piece which has been folded in the transverse direction around the folded packing-configured absorbent article. The packing wrap is subsequently joined together along its open edges so that a more or less sealed bag-like container for the absorbent article is formed.

The absorbent article to be packed individually is usually folded once or twice before the packing wrap is folded around the article. Small absorbent articles such as, for example, panty liners are sometimes also packed in an unfolded state.

One type of individual packing is described in the document GB 2,221,667 A where an absorbent article is doubled in a first step, after which a packing wrap is folded around the article. The packing wrap is finally sealed around its three sides which are open after folding.

When an individual packing of the type described in GB 2,221,667 A is to be opened, this is usually effected by the seal along one or more of the edges being broken open, after which the absorbent article can be taken out of its packing.

Another type of individual packing has separate material pieces arranged on the upper side and the lower side of a folded or unfolded absorbent article. The two material pieces are then sealed along their entire periphery, a packing wrap then being formed. These individual packings normally have a rectangular or square shape, but packings profiled according to the contour of the absorbent article are also found. Profiled individual packings are most common for small absorbent articles such as panty liners and small sanitary towels. Individual packings of the kind described can be opened in a number of different ways. For individual packings made of paper, the commonest method is quite simply to tear off one edge when the packing is to be opened.

For individual packings made of plastic films, the opening problem has often been solved by arranging a weakening of the film material along one of the edges of the individual packing, it then being possible for the film material to be torn apart along the weakening. The commonest and simplest type of weakening consists of a perforation along a length of the periphery of the individual packing. It is usual to arrange the perforation parallel and adjacent to one of the edges of the packing wrap, so that an edge strip is quite simply torn off when the packing is opened. In this connection, the perforation should be arranged in both the front and rear material pieces of the packing wrap and also suitably extend all the way from one edge to the opposite edge of the packing.

Edge seals which can be broken open are also found. The edge seal along part of the periphery of the individual packing is then weaker than remaining parts of the edge seal, so that this part of the periphery can easily be broken open when the individual packing is to be opened.

A type of individual packing for absorbent articles is described in patent EP 0,865,264.

The packing in accordance with this document is rectangular and comprises a special opening tab. The opening tab is connected to the rest of the packing along one of its edges, while the opposite edge is free and constitutes the opening location of the packing. The free edge of the opening tab extends over one surface of the packing parallel to two of the edges of the packing.

The packing has a special openable tape tab arranged on the opening tab, intended to hold the free edge of the opening tab in place against the surface of the packing wrap. Such tape tabs are also arranged in order to facilitate closing of a used absorbent article placed inside the packing wrap before its disposal.

Tape tabs of the kind described can also serve as means for detection of the positioning of the opening. This detection possibility is advantageous when a person with reduced ability to see is to open the packing wrap as s/he can feel where the opening is located.

A tape tab on the packing wrap according to the description above nevertheless involves certain disadvantages, a first being the extra material cost the tape tab involves. A second disadvantage is that the manufacturing rate is reduced as the separate tape tabs have to be applied to the packing wrap, which also has a negative effect on the cost of the individually packed absorbent article. A third disadvantage is that tape tabs of the kind described are in principle suitable only for packings comprising an opening tab.

In spite of many improvements having been made as far as the openability of individual packings is concerned, the problem still remains of finding where on the packing the opening is located when it is to be opened.

This is a particularly irritating problem for people with impaired vision, which is not uncommon especially among elderly users of absorbent articles of the incontinence pad type.

Existing solutions using colour-markings which show where on the individual packing the opening is located are not a functional solution for weakly sighted users either.

Lastly, it is not an appropriate alternative for weakly sighted incontinent users of incontinence pads to ask another person for help with opening an individually packed absorbent article because incontinence is a particularly taboo complaint which sufferers are reluctant to reveal to people around them.

OBJECTS AND SUMMARY

A need therefore remains for an improved packing wrap for individually packed absorbent articles where the opening can be detected with the aid of the sense of touch and which is simple and inexpensive to manufacture and can be manufactured at high rates.

According to one embodiment of the present invention, a packing wrap of the kind referred to in the introduction has been produced, which packing wrap essentially eliminates the problems, especially for weakly sighted users, associated with previously known packing wraps for individually packed absorbent articles.

A packing wrap, made according to the embodiment, for an individually packed absorbent article of the above-mentioned kind is in this connection characterized mainly in that the means for tactile detection has a longitudinal extent, the means being arranged essentially parallel to the longitudinal extent of the opening location.

According to one embodiment, in order to render detection of the longitudinal extent of the opening location more effective, the means for tactile detection extends over a distance which exceeds 30% of the length of the opening location, preferably more than 50% of the length of the opening location.

According to another embodiment, the opening location comprises a weakening in at least one of the first and second material pieces of the packing wrap, the weakening which can be broken open being arranged along a line.

In an alternative embodiment of the invention, the weakening comprises a perforation arranged in at least one of the first and second material pieces of the packing wrap. According to one embodiment, the weakening is arranged in both the first and the second material piece, at least one of the material pieces having means for tactile detection adjacent to the weakening.

In an alternative embodiment, the weakening can comprise a join in the packing material.

In one embodiment of the invention, the join constitutes the means for tactile detection.

In accordance with one embodiment of the invention, the means for tactile detection can be arranged along only one side of the weakening.

According to a preferred embodiment of the invention, the means for tactile detection comprises at least one embossed region. This embodiment is particularly advantageous when the packing material consists of a plastic film or a paper material because it is then possible to emboss directly on the packing material, and no extra material cost arises.

In an alternative embodiment of the invention, the means for tactile detection comprises at least one extra material strip. The material strip is then connected to the material of the packing wrap in a suitable way.

The extra material strip can comprise a nonwoven material, a paper material, a foam material or another suitable material. It is important that the extra material strip differs from the material of the packing wrap as far as tactile detection is concerned.

According to a preferred embodiment, the extra material strip can comprise one or more thread-shaped materials. Thread-shaped materials are easy to detect with the sense of touch in the fingers and simple to handle in a manufacturing machine at high machines rates. In accordance with one embodiment of the invention, the means for tactile detection is arranged by at least one surface on the packing wrap being coated with a material which has higher or lower friction than the other surfaces of the packing wrap. Frictional differences between different adjacent surfaces are extremely easy for a weakly sighted person to detect by means of the sense of touch.

According to a particularly preferred embodiment, the packing wrap has a rectangular shape. In this connection, the two material pieces of the packing wrap extend outside the periphery of the absorbent article and are interconnected in the area outside the periphery of the absorbent article. The two material pieces can consist of one larger material piece which has been folded around the packing-configured absorbent article or of two completely separate material pieces.

One embodiment of the invention is characterized in that the packing wrap has a rectangular shape, and in that the weakening runs essentially parallel and adjacent to one of the edges of the packing wrap in at least one of the first and second material pieces of the packing wrap. The connection between the first material piece and the second material piece of the packing wrap along the edge then has a different texture compared with the connection along the other edges of the packing wrap, the different connection constituting the means for tactile detection.

Another embodiment of the invention has a rectangular shape and is further characterized in that the weakening constituting the opening location comprises that part of the connection between the first material piece and the second material piece of the packing wrap which has a different texture. The said connection can be broken open and constitutes both the opening location of the packing wrap and its means for tactile detection.

BRIEF DESCRIPTION OF FIGURES

The invention will be described in greater detail below with reference to the illustrative embodiments shown in accompanying figures, in which.

DETAILED DESCRIPTION OF PREFERRED EMBODIMENTS

The invention relates to a packing wrap for an absorbent article of the sanitary towel, panty liner, incontinence pad or baby diaper type.

Figure 1:
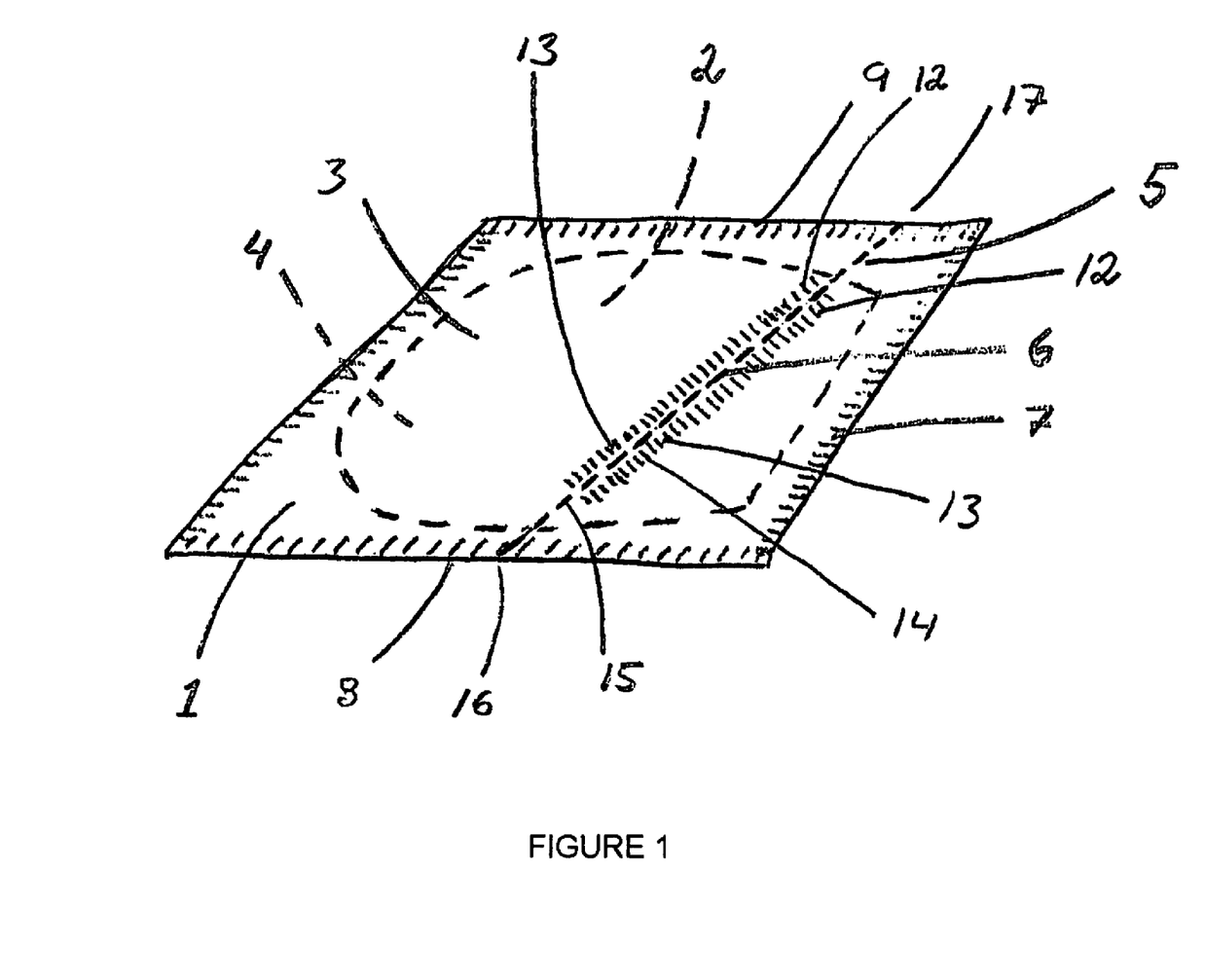
FIG. 1 shows a closed packing wrap enclosing an incontinence pad according to a first embodiment.
Figure 2:
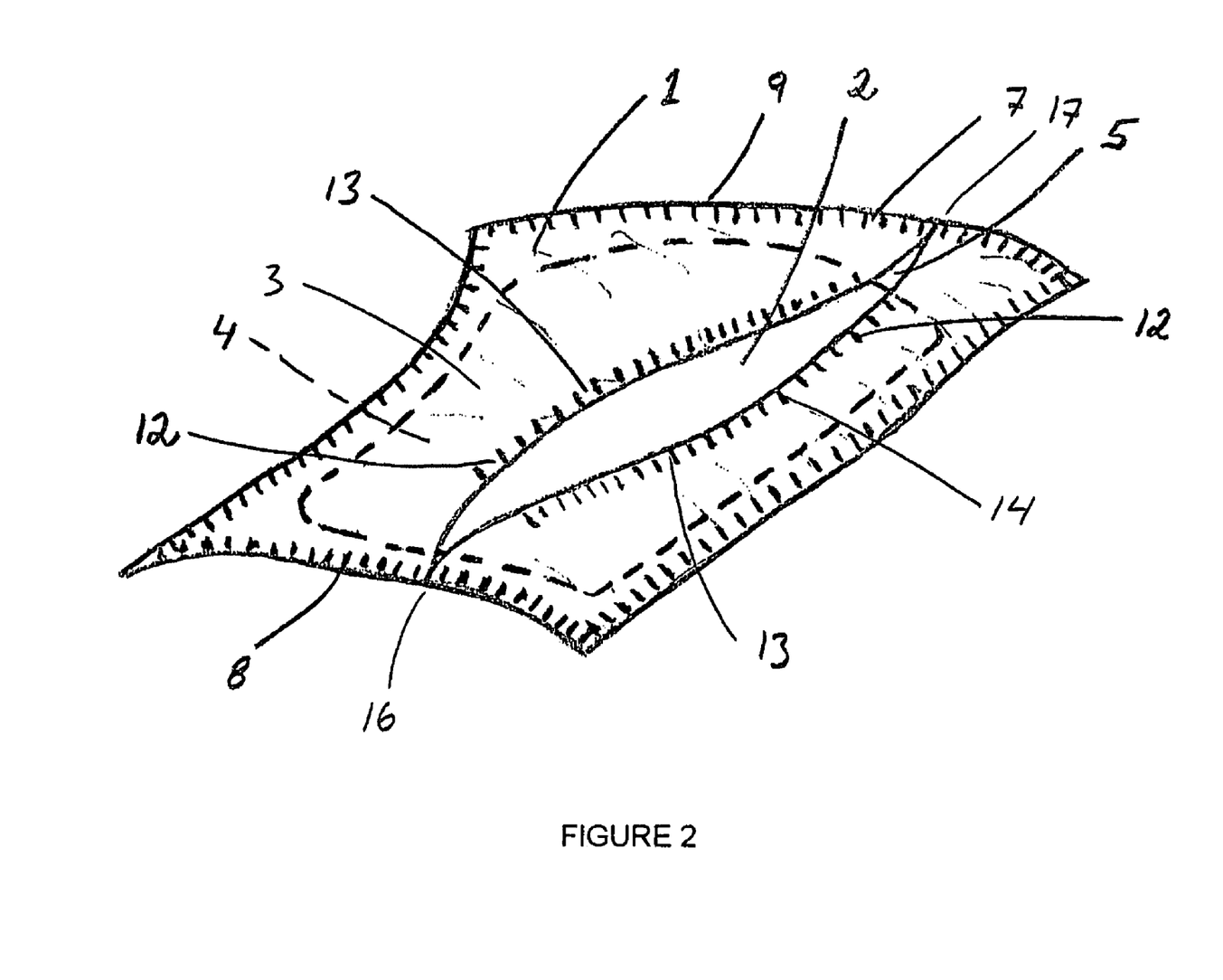
FIG. 2 shows the packing wrap according to FIG. 1 in a partly opened state.

The packing wrap 1 shown in FIGS. 1 and 2 relates to a packing wrap 1 for an incontinence pad 2 intended for lighter forms of incontinence, so called light incontinence.

The incontinence pad 2 inside the packing wrap 1 has a conventional construction and comprises a first, liquid-permeable covering layer arranged on that side of the incontinence pad 2 which is intended to face the wearer during use, a second, liquid-tight covering layer arranged on that side of the incontinence pad 2 which is intended to face away from the wearer during use, and an absorbent body enclosed between the two covering layers.

The absorbent body can be constructed from one or more layers of cellulose fluff pulp. In this connection, cellulose fluff pulp can be mixed with fibres or particles of a highly absorbent polymer material of the kind which chemically binds great quantities of liquid during absorption while forming a liquid-containing gel. The absorbent body can also comprise highly absorbent polymer material arranged in one or more layers inside the absorbent body or adjacent to the surface or surfaces of the absorbent body.

The absorbent body can also include components of a non-absorbent nature in order to improve the properties of the absorbent body. Examples of such components are bonding fibres, shape-stabilizing components, strengthening fibres or the like.

Various types of layer and material provided for improved spreading of liquid can also form part of the absorbent body.

The absorbent body can of course also comprise other types of absorption material, such as absorbent nonwoven materials, absorbent foams, textile materials, peat, or mixtures of different kinds of absorption material. Special layers for rapidly receiving large quantities of liquid and temporarily storing this liquid in order then to discharge the temporarily stored liquid to other parts of the absorbent body can also be included in incontinence pads of the kind described. These receiving layers are then normally arranged between the liquid-permeable covering layer and the absorbent body of the incontinence pad.

The two covering layers of the absorbent article project past the edges of the absorbent body, the projecting portions of the covering layers being interconnected around the periphery of the absorbent body, for example, by means of gluing, sewing, or by welding using heat or ultrasound.

The material in the liquid-permeable covering layer can be of any suitable kind. Examples of common liquid-permeable covering materials are various types of bonded nonwoven materials, perforated plastic films, net and also open-cell or perforated foam materials. Liquid-permeable covering materials which consist of continuous thin fibres which extend mainly in the longitudinal direction or transverse direction of the absorbent article are also found. Laminates consisting of two or more of the abovementioned possible covering materials are also common, as are coverings consisting of different materials in different parts of the surface.

An incontinence pad which comprises absorbent bodies with particularly great strength and wear-resistance can even function without any extra liquid-permeable covering layer being required on that side of the incontinence pad which faces the wearer during use.

The liquid-tight covering layer suitably comprises a thin plastic film, or of a nonwoven material which has been made liquid-tight by coating or treatment with a liquid-resistant material. Other types of liquid-blocking material can of course also be used, such as, for example, plastic foam with closed cells, various liquid-blocking laminates etc. In order that the incontinence pad 2 will feel airy and pleasant to wear, it is suitable for the liquid-tight covering layer to have a certain permeability for air and water vapour. The liquid-tight covering layer can also be integrated in the absorbent body and comprise, for example, a skin-like surface on an absorbent foam body.

On the side which is intended to face away from the wearer during use, the incontinence pad 2 is provided with a fastening arrangement for fixing to the briefs of the wearer. The fastening arrangement can comprise one or more longitudinal adhesive strands, or of what are known as hook and loop surfaces or the like. When the fastening arrangement comprises adhesive strands, these are usually covered by a release-agent-treated protective layer.

In connection with or immediately prior to the incontinence pad 2 being placed in its packing wrap 1, the incontinence pad 2 has been folded around two transverse folding lines. In this connection, the folding has been arranged so that each folded part constitutes approximately a third of the length of the incontinence pad 2, the folded incontinence pad 2 having a length corresponding to a third of the total length of the incontinence pad 2. The folding has been carried out so that that surface of the incontinence pad 2 which is intended to face away from the wearer during use of the incontinence pad 2 is the outwardly exposed surface when the incontinence pad 2 is folded.

Packing configurations where the incontinence pad 2 is doubled or unfolded are also found.

The packing wrap 1 shown in FIGS. 1 and 2 comprises a first material piece 3 arranged over one surface of the incontinence pad 2 when the latter is folded into its packing configuration, and a second material piece 4 arranged over the second surface of the incontinence pad 2.

The two material pieces 3, 4 extend outside the periphery of the incontinence pad 2 and are interconnected along the entire periphery of the packing wrap 1. The connection 7 suitably comprises a thermal weld, an ultrasonic weld or the like.

For some types of packing wrap 1, the first and second material pieces 3, 4 can comprise one larger material piece which has been folded around the incontinence pad, the connection 7 along one of the edges of the packing wrap 1 consisting of the said fold.

The packing wrap 1 can comprise a number of different materials such as plastic film, paper, nonwoven or the like.

The packing wrap 1 comprises an opening location 5 which extends along a line essentially diagonally over the first material piece 3, the opening location 5 comprising a weakening 6 in the material piece 3 in the form of a perforation 15. Alternative methods of weakening the opening location 5 are also conceivable, such as, for example, making the material piece 3 thinner.

The opening location can be arranged alternatively in either of the material pieces 3, 4 or in both material pieces 3, 4.

It is also possible for the opening location 5 to comprise a slit in the material piece 3, in which case it is suitable that the slit comprises some kind of overlapping material in order to prevent impurities of various kinds entering the packing wrap 1.

The opening location 5 can, as shown in FIGS. 1 and 2, extend across and essentially diagonally over the whole packing wrap 1. It is also conceivable for the opening location 5 to extend over a shorter distance than over the whole packing wrap 1.

The opening location 5 can also extend along a line parallel to any one of the edges of the packing wrap 1, or along a curved line arranged diagonally over the packing wrap 1, or the like.

FIG. 1 shows a packing wrap 1 where the opening location 5 is closed, while FIG. 2 shows a corresponding packing wrap 1 where the opening location 5 is open and where the incontinence pad 2 is visible inside the packing wrap 1.

The packing wrap 1 is opened by the weakening 6 being broken open, that is to say the material piece 3, 4 which comprises the opening location 5 is torn in two along the perforation 15.

Figure 3:
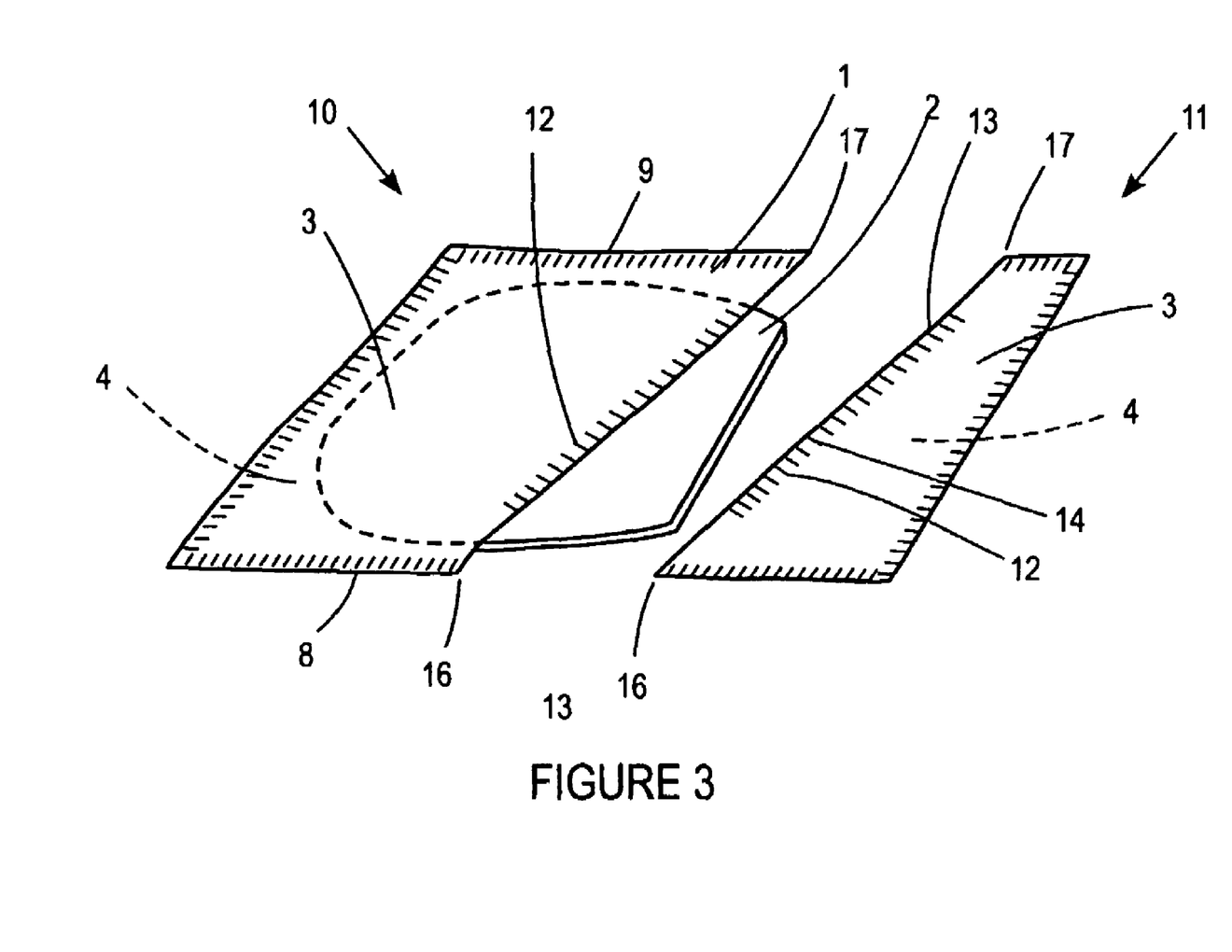
FIG. 3 shows an opened packing wrap containing a packed incontinence pad according to a second embodiment.

FIG. 3 shows an embodiment of the packing wrap 1 in an opened state, where the opening location 5 extended over both the first and the second material piece 3, 4 before the packing wrap 1 was opened. The opening location 5 extends over both material pieces 3, 4 from one edge 8 of each material piece 3, 4 to the opposite edge 9 of each material piece 3, 4. The respective extents of the opening location 5 in the first and the second material piece 3, 4 are then suitably arranged so that they extend essentially parallel over each material piece 3, 4 from a common starting point 16 at one edge 8 to a common terminating point 17 at the opposite edge 9.

When such a packing wrap 1 is opened, the packing wrap 1 is usually divided into two parts 10, 11, but it is also conceivable for the two parts 10, 11 to continue to hold together at the starting point 16 or the terminating point 17 after the packing wrap 1 has been opened.

A packing wrap 1 according to one embodiment of the invention is characterized mainly in that it comprises means 12 for tactile detection of the position of the opening location 5.

The packing wrap 1 shown in FIGS. 1, 2 and 3 is distinguished in that the opening location 5 can be detected with the aid of the sense of touch. In this connection, the packing wrap 1 comprises embossed regions 13 adjacent to the opening location 5. The embossed regions 13 have a width and a length and run essentially parallel to the opening location 5, an embossed region 13 running on each side of the opening location 5.

In alternative embodiments, it is conceivable that only one embossed region 13 runs parallel to the perforation 15 of the opening location 5 along only one of its sides.

It is also conceivable to use a number of shorter embossed regions 13 with unembossed regions between the embossed regions 13, the embossed regions 13 being arranged along one side or both sides of the opening location 5.

The embossed regions 13 extend along roughly 60% of the length of the perforation 15.

The embossed regions 13 do not have to extend along the entire length of the perforation 15, but it is suitable that they extend over more than 30% of the total length of the opening location, preferably more than 50% of the length.

The embossed regions 13 are arranged so that they differ from the texture of the embossed material piece 3, 4 as far as touch is concerned, it being possible for the embossed regions 13 and adjacent perforation 15 to be detected easily with the sense of touch in, for example, the fingers of the person who is to open the packing wrap 1.

Embossed regions 13 are brought about by the material piece 3, 4 passing through an embossing unit in a manufacturing step before the material piece 3, 4 is applied over the incontinence pad 2. In this connection, the embossing unit has a male part comprising projecting embossing bodies and a female part comprising sunken embossing recesses, the male part and the female part being arranged synchronously. When that region of the material piece 3, 4 which is to be embossed passes between the male part and the female part of the embossing unit, the material piece 3, 4 is deformed plastically, permanently deformed protuberances being obtained in the material. Alternative ways of producing embossed regions are also conceivable.

In the illustrative embodiment, the pattern of the embossed regions 13 consists of straight embossed lines 14 arranged at right angles to the opening location 5.

The embossing pattern can vary within wide limits and can consist of, for example, lines parallel to the opening location 5, a number of small circles arranged parallel to the opening location or the like.

Embossing involves the great advantage that no costly extra material has to be added, because it is the already present material piece 3, 4 which is modified.

The material piece 3, 4 must, at least in the area to be embossed, comprise an embossable material. Suitable embossable materials are various types of plastic film, paper or the like.

Figure 4:
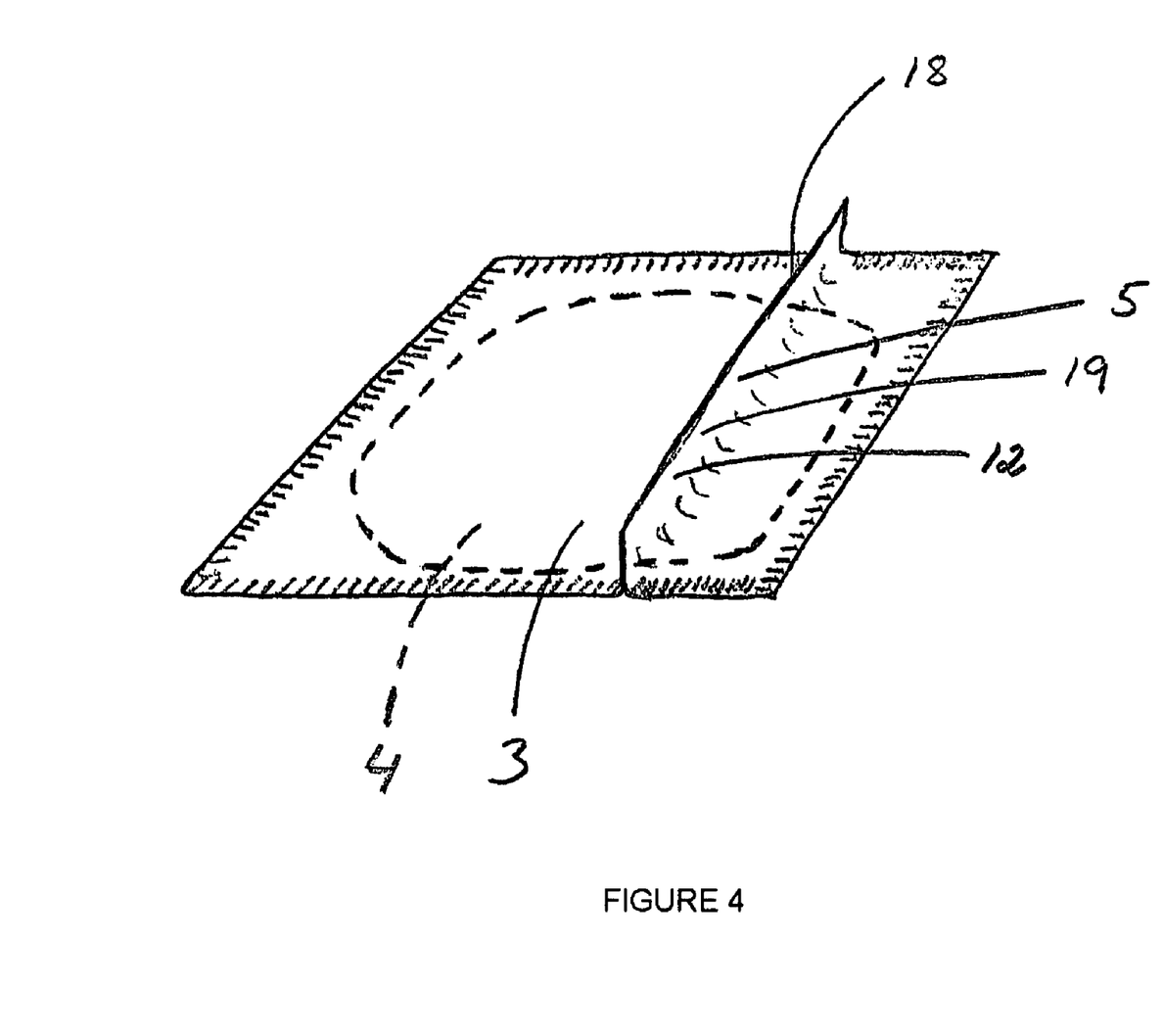
FIG. 4 shows a closed packing wrap enclosing a packed incontinence pad according to a third embodiment.

FIG. 4 shows another embodiment of the invention. In this embodiment, the opening location 5 comprises an openable join 18 in the first material piece 3. The join 18 is designed as a ridge 19 which projects from the surface of the material piece 3, the ridge 19 also constituting the means for tactile detection 12 and being easy to detect with the aid of the sense of touch.

Alternative designs of the join 18 are also conceivable; for example, the join 18 can be what is known as a lap join. A lap join means that the component parts of the material piece 3 overlap one another at the join 18. Such a join 18 is slightly more difficult to detect than a join 18 which consists of a ridge 19, for which reason an embossed region 13 or the like is advantageous adjacent to such an overlapping join 18.

Another advantage of the embodiment according to FIG. 4 is that the packing can be opened easily by bending the packing containing an article so that the surface comprising the ridge 19 has a convex configuration oriented at right angles to the ridge 19. The join 18 is then subjected to a tensile stress which means that it breaks, the packing then opening.

Figure 5:
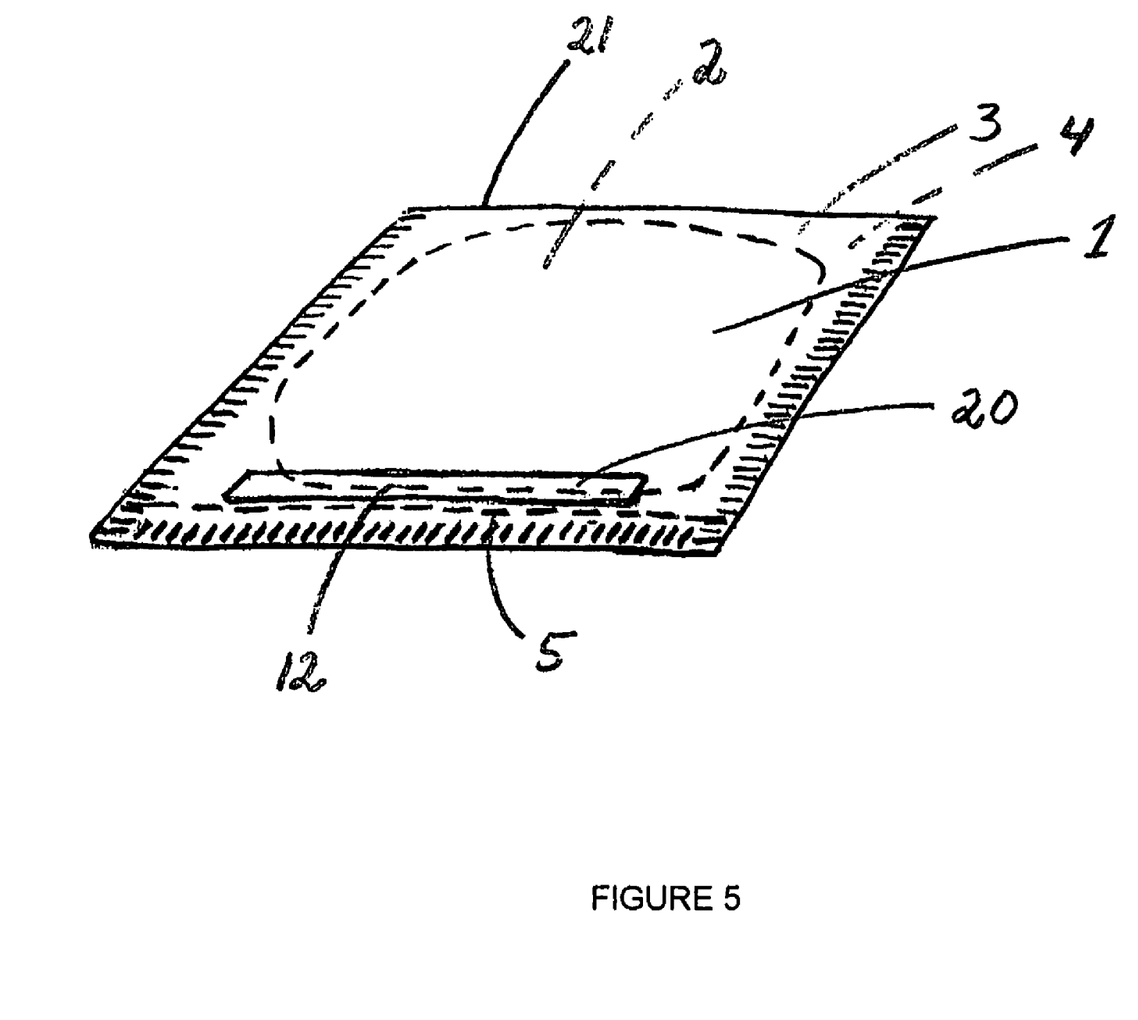
FIG. 5 shows a packing wrap according to another embodiment.

FIG. 5 shows another embodiment of the invention. The packing wrap 1 has a rectangular shape. The first and second material pieces 3, 4 comprise one larger material piece which has been folded around the incontinence pad 2, after which three of the edges of the packing wrap 1 have been connected by means of a thermal weld, an ultrasonic weld or the like. The connection along the fourth edge of the packing wrap 1 comprises the said fold 21.

In accordance with this embodiment, the packing wrap 1 has been provided with an extra material strip 20 constituting the means for tactile detection 12. The material strip 20 extends essentially parallel to the opening location 5, over roughly 70% of its length.

The material strip 20 is connected to the packing wrap 1 by means of gluing, thermal welding, ultrasonic welding or the like on the outwardly oriented surface of the packing wrap 1.

The material strip 20 comprises a material which has different properties as far as touch is concerned compared with the material of the packing wrap 1. Suitable materials are plastic strips with different friction properties, nonwoven strips, paper strips or the like.

The material strip 20 can of course also have another type of different texture in relation to the material of the packing wrap 1; it can, for example, comprise an embossed material strip 20, a material strip 20 which is considerably more rigid than the material of the packing wrap 1, a material strip 20 which is thicker than the material of the packing wrap 1, or one which is different in another way.

The material strip 20 can also comprise a thread-shaped material which can be detected easily with the aid of the sense of touch in the fingers. It is possible, for example, for one or more threads to be arranged so that they extend essentially parallel to the opening location 5 of the packing wrap 1. The threads can comprise textile threads, rubber threads or the like, which differ from the material of the packing wrap 1 as far as touch is concerned.

Instead of a material strip 20, it is also conceivable to coat the material of the packing wrap 1 with a material which has different properties as far as touch is concerned compared with the material of the packing wrap 1. The coating can comprise, for example, rubber coating having increased friction, solid particles which have been fixed in a glue film so that the surface feels rough, or the like.

Figure 6:
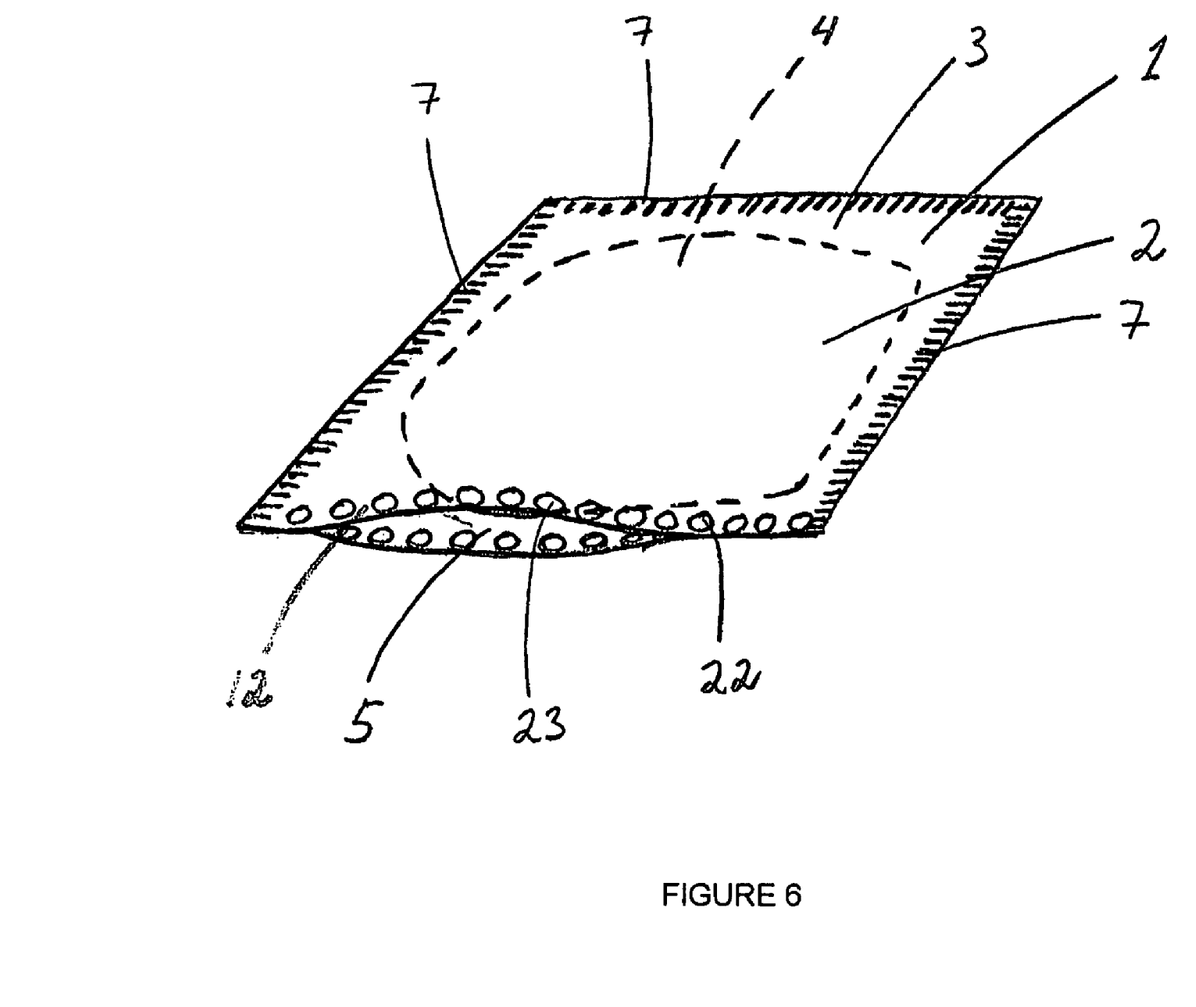
FIG. 6 shows a packing wrap according to one embodiment.

The packing wrap 1 according to FIG. 6 is shown in a partly opened state. The packing wrap 1 comprises a first material piece 3 arranged over one surface of the incontinence pad 2 when this is folded into its packing configuration, and a second material piece 4 arranged over the other surface of the incontinence pad 2.

The two material pieces 3, 4 extend outside the periphery of the incontinence pad 2 and are interconnected along the entire periphery of the packing wrap 1.

The packing wrap 1 has a first type of connection 7 along three of the four edges of the packing wrap 1 and a second type of connection 22 along the fourth edge. The connections 7, 22 suitably comprise a thermal weld, an ultrasonic weld or the like. The connection 22 is less strong than the other connections 7, the connection 22 being openable and constituting the opening location 5 of the packing wrap 1.

The connection 22 also has a different pattern 23 compared with the connections 7 along the other edges of the packing wrap 1. The different pattern 23 constitutes the means 12 of the packing wrap for tactile detection of the opening location 5.

A packing wrap 1 where one connection 22 is weaker than the other connections 7 and the means 12 for tactile detection comprises an extra material strip, a thread-shaped material, a coating or the like is also conceivable.

Another alternative is to use the same connection pattern for all four edges of the packing wrap but to select a narrower or wider pattern along the edge which constitutes the opening location.

Figure 7:
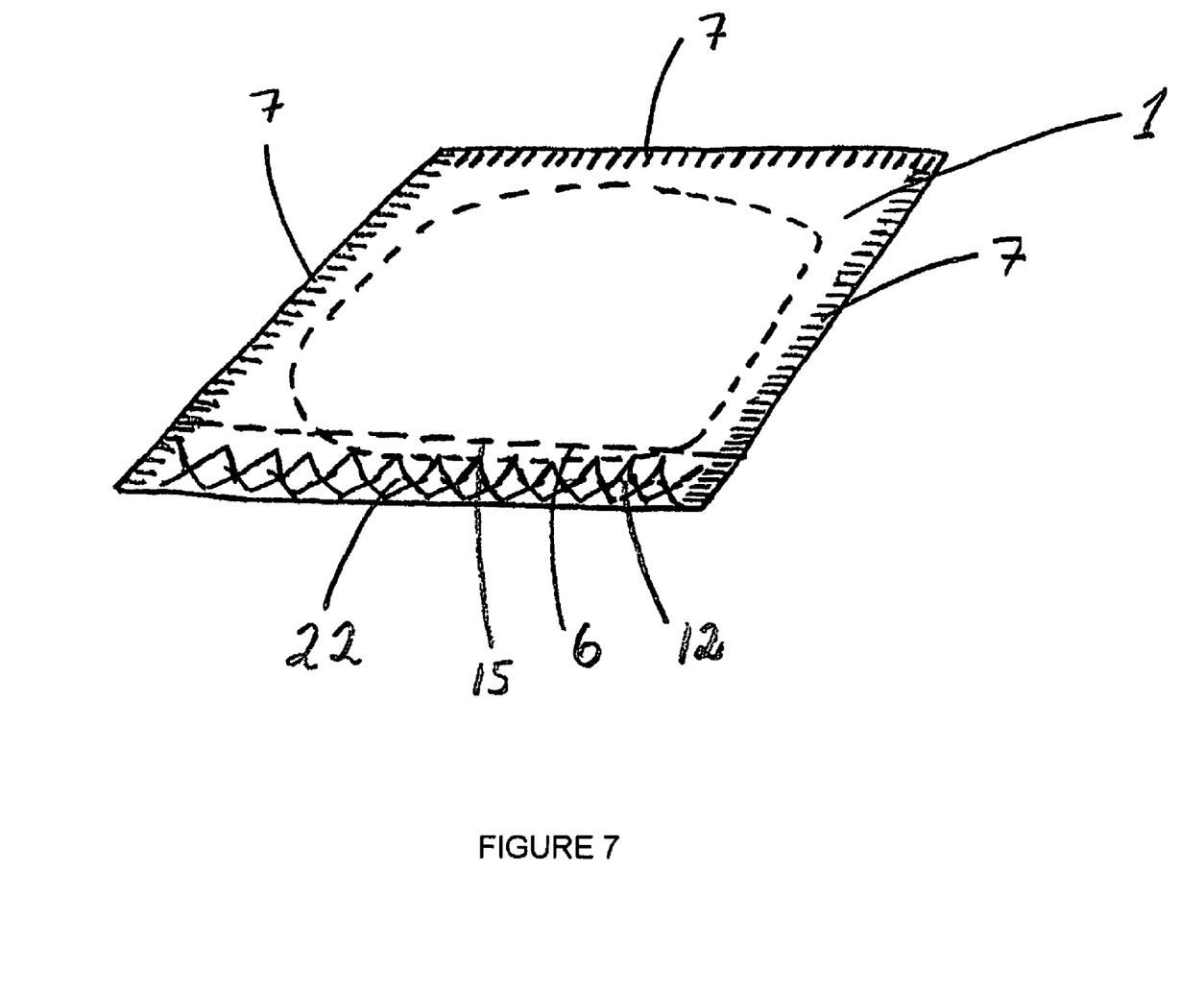
FIG. 7 shows a packing wrap according to another embodiment.

FIG. 7 shows a packing wrap 1 according to another embodiment of the invention. The packing wrap 1 has a first type of connection 7 along three edges and a second type of connection 22 along its fourth edge. The connection 22 differs from the connection 7 in that it has a different pattern. The different connection 22 then constitutes the means 12 for tactile detection. The opening location 5 comprises a weakening 6 in the form of a perforation 15 in the material of the packing wrap 1 or the like.

The invention also comprises all conceivable combinations of the illustrative embodiments described.

Furthermore, the invention is not limited to the illustrative embodiments referred to above but is of course applicable for other embodiments within the scope of the following patent claims.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A packing wrap for enclosing an individual absorbent article, the packing wrap comprising:
    a first material piece arranged over a first surface of the absorbent article and a second material piece arranged over a second surface of the absorbent article,
    an opening location having a longitudinal extent on at least one of the first material piece and the second material piece, wherein the opening location is weakened such that it will tear prior to adjacent areas on the respective material piece,
    the first material piece and second material piece are interconnected to each other along an entire outer periphery of the packing wrap,
    a central region positioned within the outer periphery and located on one of the first material sheet or the second material sheet, and
    a tactile region, located in the central region and spaced from the outer periphery, capable of tactile detection of the position of the opening location on the packing wrap, the tactile region arranged at the opening location, and the tactile region has a longitudinal extent and is arranged essentially parallel to the longitudinal extent of the opening location,
    wherein the tactile region constitutes a surface area, and the surface area has a different texture than adjacent surfaces and wherein the tactile region extends along more than 30% of the length of the opening location, and
    wherein the first material piece and the second material piece continuously extend along the outer periphery after tearing of the opening location.

2. The packing wrap according to claim 1, wherein the weakened location includes a perforation arranged in at least one of the first and second material pieces of the packing wrap.

3. The packing wrap according to claim 1, wherein the packing wrap has a rectangular shape, the two material pieces of the packing wrap extending outside a periphery of the absorbent article.

4. The packing wrap according to claim 1, wherein the absorbent article is a sanitary towel, a panty liner, or an incontinence pad.

5. The packing wrap according to claim 1, wherein the tactile region includes a separate piece of material that has a different texture than adjacent surfaces.

* * * * *